United States Patent [19]

Hammarlund

[11] Patent Number: 5,711,292
[45] Date of Patent: Jan. 27, 1998

[54] MEANS FOR PRODUCING AN AEROSOL

[75] Inventor: Nils Hammarlund, Sollentuna, Sweden

[73] Assignee: AGA Aktiebolag, Lidingo, Sweden

[21] Appl. No.: 716,203

[22] PCT Filed: Jan. 31, 1995

[86] PCT No.: PCT/SE95/00087

§ 371 Date: Sep. 11, 1996

§ 102(e) Date: Sep. 11, 1996

[87] PCT Pub. No.: WO95/25556

PCT Pub. Date: Sep. 28, 1995

[30] Foreign Application Priority Data

Mar. 18, 1994 [SE] Sweden ................................. 9400927

[51] Int. Cl.$^6$ ............................................. A61M 11/00
[52] U.S. Cl. ........................... 128/200.21; 128/200.18; 128/200.14
[58] Field of Search ..................... 128/200.18, 200.21, 128/200.14, 200.16

[56] References Cited

U.S. PATENT DOCUMENTS

| | | | |
|---|---|---|---|
| 2,826,454 | 3/1958 | Coanda | 128/200.18 |
| 4,512,341 | 4/1985 | Lester | 128/200.18 |
| 4,588,129 | 5/1986 | Shanks | 128/200.18 |
| 4,757,812 | 7/1988 | Arborelius, Jr. | |
| 4,792,097 | 12/1988 | Kremer et al. | 128/200.18 |

*Primary Examiner*—Vincent Millin
*Assistant Examiner*—William J. Deane, Jr.
*Attorney, Agent, or Firm*—Pearne, Gordon, McCoy & Granger LLP

[57] ABSTRACT

The invention relates to a device for producing a fine inhomogeneous aerosol, comprising a liquid container (1) and a liquid-conducting pipe (2) whose outlet orifice (6) at one end is located in a first disc (5) and whose other end extends towards the container bottom, wherein the pipe-outlet orifice (6) is located in the first disc (5) in the proximity of and is directed at least generally at right angles to a second disc (4). The device includes a gas conduit (3) which terminates in the pipe (2) in the proximity of its outlet orifice (6) in the first disc (5). The conduit (3) leads to the pipe (2) and draws liquid through the pipe by suction and, in the proximity of the pipe orifice generates a first aerosol which is directed towards the second disc (4) and forms thereon a film which spreads radially across the second disc (4) and is therewith thinned out, this film shattering at the border edges of the second disc (4) into droplets which form in the gas a second inhomogeneous aerosol. The device is used for producing a fine inhomogeneous aerosol for medical treatment purposes. A helium-containing gas can be used as the propellant gas.

10 Claims, 1 Drawing Sheet

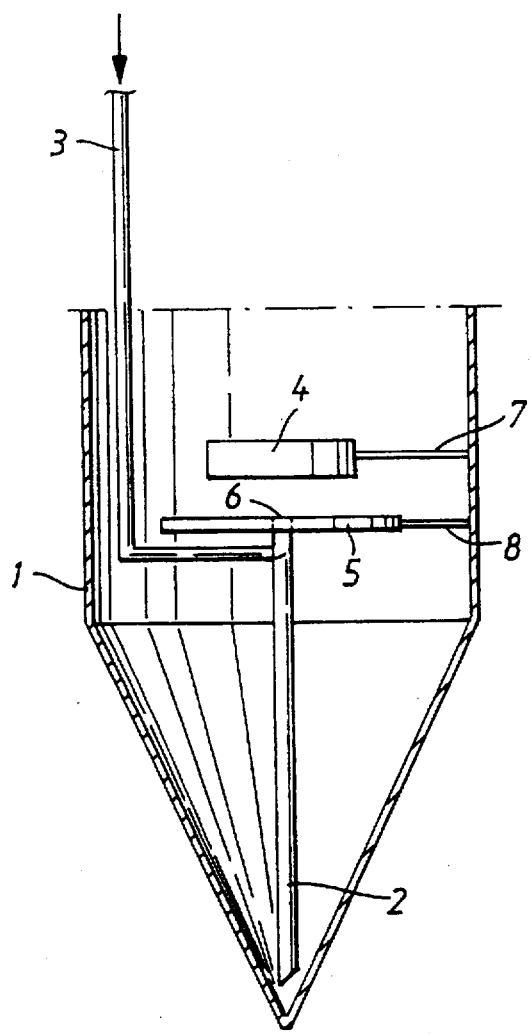

MEANS FOR PRODUCING AN AEROSOL

BACKGROUND OF THE INVENTION

The present invention relates to a device for producing a very fine non-homogeneous aerosol, such device normally being referred to as a nebulizer. The invention also relates to the use of the nebulizer to produce a non-homogeneous aerosol. The device is particularly useful in medical treatment, i.e. for administering medicines or drugs in aerosol form.

European Patent Specification 0191018 describes a nebulizer for producing an homogenous aerosol. The known device includes a container in which two mutually parallel and mutually spaced discs are arranged, of which discs one has a larger area than the other. The smaller of the discs has a central opening through which gas is caused to flow in a direction towards the opposing disc. This disc, the smaller disc, also has liquid openings placed outside the gas opening. The gas delivered to the container generates, between the disc, a subpressure which causes liquid to flow towards the opposing larger disc. Utilizing the so-called coanda-effect, there is produced on the larger of the discs a liquid film which is transformed into liquid droplets of essentially equal size at the edges of the disc, i.e. homogeneous or uniformly-sized liquid droplets which form the aerosol together with the gas.

SUMMARY OF THE INVENTION

One object of the present invention is to provide a highly efficient nebulizer with which non-homogeneous aerosols, i.e., aerosols comprised of liquid droplets of non-uniform or different sizes, can be produced.

Another object is to provide a nebulizer with which the percentage of minute droplets of liquid is high.

These object are achieved in accordance with the invention by means of a device which functions to produce a fine non-homogeneous aerosol and which includes a liquid container and a liquid passageway whose one end discharges in a first disc and whose other end extends towards the container bottom, wherein the discharge orifice of the liquid passageway in the first disc is located in the proximity of a second disc and is directed at least generally at right angles to said second disc.

The device includes a liquid container, a liquid conducting pipe whose outlet orifice is disposed in a first disc and whose other end extends toward the container bottom. The outlet orifice is located adjacent to a second disc. The device further includes a gas conduit which is connected to a pressurized gas container and which terminates in the pipe proximal the outlet orifice.

In further accordance with the present invention, the second disc is smaller than the first disc and the gas conduit leads gas to the pipe and draws liquid through the passageway and generates a first aerosol adjacent the outlet orifice. The first aerosol is directed toward and impinges upon the second disc and forms a radially-spreading film thereon. The film thins and breaks down at the border edges of the second disc to form droplets. The droplets form in the gas a second non-homogeneous aerosol which combines with the portion of the first aerosol that doesn't impinge upon the second disc.

BRIEF DESCRIPTION OF THE DRAWINGS

The invention will now be described in more detail with reference to an exemplifying embodiment thereof and also with reference to the accompanying drawing, the single FIGURE of which is a schematic vertical section view of the inventive device.

DETAILED DESCRIPTION OF THE PREFERRED EMBODIMENT

The illustrated device includes a container 1, which may have a circular cross-section, and a part which tapers conically towards the bottom of the container 1. A liquid conducting pipe or conduit 2 extends from the bottom of the container through a relatively large, first disc 5 where it forms a liquid discharge orifice 6. A second disc 4 is mounted above the first disc 5 parallel therewith and at a distance of at most 2 mm therefrom. The discs 4 and 5 are held fixed in relation to one another with the aid of respective arms 7 and 8, which connect the discs to the container wall. Only one arm is shown for each disc. A gas pipe or conduit 3 opens into the pipe 2 and is directed in the pipe towards the outlet orifice 6 thereof. Although not shown, the other end of the gas pipe 3 is provided with means for connecting the pipe to a source of gas under pressure. The mutually facing surfaces of the discs 4 and 5 may be parallel with one another, for instance plane-parallel, or curved, for instance spherically curved, wherein one surface is convex and the other concave. According to one embodiment, the first disc 5 is flat and the opposing surface on the second disc (4) is curved. The radius of curvature of the surface in this latter embodiment and also the radii of curvature of the curved parallel surfaces is at least 50 mm. The discs are preferably circular in shape, but may also have any other suitable geometrical shape, for instance a rectangular or elliptical shape.

Liquid is delivered to the container when the device is to be used. The liquid may be purely a medicine, medicament, or a solvent solution and/or solvent dispersion thereof. Gas is delivered to the nebulizer from a gas supply (not shown) through the pipe 3. Because the outlet orifice of the pipe 3 is directed towards the orifice 6 of the pipe 2 and flows at a high rate, the liquid from the container will be sucked or drawn through the passageway 2 and forms together with the gas a dispersion which leaves through the orifice 6.

The major part of the aerosol formed will impinge on the opposing second disc 4. Only a small part of the liquid particles of the aerosol, i.e. the smallest particles, will accompany that part of the gas flow which deviates to one side. Those liquid particles that impinge on the second surface will spread towards its periphery while thinning out. The liquid film will shatter at the border of the second disc and form small liquid droplets of varying sizes.

The particles formed at the border of the second disc will accompany the gas flow from the orifice 6 in the first disc 5. Due to their mass of inertia, those particles that have a high mass will impinge on the side wall of the container 1. It is possible to remove to some extent liquid particles above a given size, by changing the distance between the bordering edge of the second disc and the container wall.

Another method of obtaining small particles is to use a light gas as the aerosol producing propellant gas. It has been found that smaller particles are obtained when neon, and particular helium, is used as the propellant gas than when air is used, air being the propellant gas normally used in producing aerosols for medical use. A preferred propellant gas is thus a mixture of neon and/or helium with oxygen. The oxygen concentration will lie within a suitable interval for respiration purposes.

I claim:

1. A device for producing a fine non-homogeneous aerosol, comprising a liquid container (1), a liquid-conducting pipe (2) whose outlet orifice (6) is located in a first disc (5), whose other end extends towards the bottom of the container (1) and which defines a passageway, wherein the outlet orifice (6) of the liquid-conducting pipe (2) in the first disc (5) is located in the proximity of, and directed generally at right angles to, a second disc (4), wherein the device includes a gas conduit (3) which is connected to a source of pressurized gas outside the container (1) and terminates in the pipe (2) near the outlet orifice (6), the second disc (4) is smaller than the first disc (5), wherein the gas conduit (3) directs gas to the pipe (2) and thereby draws liquid through the passageway and generates, adjacent the pipe outlet orifice, a first aerosol which is directed towards the second disc (4), wherein the large liquid particles of the first aerosol impinge on the second disc (4) and form thereon a film which spreads radially over the second disc (4) and is therewith thinned out and breaks down at the border edges of the second disc (4) to form droplets which form in the gas a second non-homogeneous aerosol which combines with a portion of the first aerosol that does not impinge on the second disc (4).

2. A device according to claim 1, wherein one of the discs (4, 5) has a concave surface and the opposing disc (5 or 4) has a convex surface, said surfaces facing towards one another.

3. A device according to claim 1, wherein the second disc (4) has a convex surface which faces towards the first disc (5).

4. A device according to claim 3, wherein the radius of curvature of the convex surface is at least 5 cm.

5. (amended) A device according to claim 1, wherein the smallest distance between the discs is at most 2 mm.

6. A device according to claim 5, wherein the smallest distance between the discs is 0.5–0.8 mm.

7. A device according to claim 1, wherein the device is connected to a source of helium-containing gas.

8. A device according to claim 7, wherein the gas source is comprised of helium and oxygen.

9. A method for producing a fine, non-homogeneous aerosol for medical treatment from a device, said device having a liquid container, a liquid-conducting pipe having an outlet orifice located in a first disc and whose other end extends toward the bottom of the container, the outlet orifice being located proximal to and directed toward a second disc, said device further including a gas conduit which is connected to said pipe adjacent said outlet orifice, the method comprising the steps of:

directing gas through the gas conduit and the liquid-conducting pipe to thereby draw fluid through the pipe from the liquid container and generate a first aerosol;

directing the first aerosol toward said second disc such that large particles from said first aerosol impinge upon said second disc and form a film thereon, a portion of said first aerosol comprising relatively lighter particles flowing around said second disc;

thinning out said film and, at edges of said second disc, forming liquid droplets of non-uniform size that combine with said portion of said first aerosol to define a non-homogeneous aerosol.

10. The method according to claim 9, wherein said first disc is smaller than said second disc, and said method produces an aerosol for inhalation.

* * * * *